United States Patent [19]

Maranhão

[11] Patent Number: 5,874,059
[45] Date of Patent: Feb. 23, 1999

[54] MICROEMULSIONS LABELLED WITH RADIOACTIVITY USED AS MEANS FOR TARGETING NEOPLASTIC CELLS

[75] Inventor: Raul Cavalcante Maranhão, São Paulo, Brazil

[73] Assignee: Fundacao E.J. Zerbini, Sao Paulo, Brazil

[21] Appl. No.: 688,611

[22] Filed: Jul. 30, 1996

Related U.S. Application Data

[63] Continuation-in-part of Ser. No. 388,147, Feb. 13, 1995, abandoned, which is a continuation of Ser. No. 388,148, Feb. 13, 1995, Pat. No. 5,578,583, which is a division of Ser. No. 042,105, Apr. 1, 1993, abandoned.

[30] Foreign Application Priority Data

Apr. 2, 1992 [BR] Brazil ...................................... 9201168

[51] Int. Cl.$^6$ ........................... A61K 9/107; A61K 51/00
[52] U.S. Cl. ...................... 424/1.11; 424/400; 424/1.45; 424/1.77; 514/937
[58] Field of Search ..................................... 424/400, 450, 424/1.11, 1.21, 1.45, 1.65, 1.77; 524/937–943

[56] References Cited

U.S. PATENT DOCUMENTS 3,992,513  11/1976  Petkau et al. .
5,324,821   6/1994  Favre et al. .

FOREIGN PATENT DOCUMENTS 92-0076   1/1992   WIPO .

*Primary Examiner*—Gollamudi S. Kishore
*Attorney, Agent, or Firm*—Darby & Darby

[57] ABSTRACT

The present invention relates to a method for diagnosing neoplasms by means of injecting radioactively-labelled microemulsions into the blood circulation so as to localize neoplastic cells. This invention provides a more accurate method for detecting the presence of tumoral processes in their early stage. The Present further provides a microemulsion that, when incorporated with greater amounts of radioactive materials, not only improves the quality of the images generated but also kills the neoplastic cells.

6 Claims, No Drawings

MICROEMULSIONS LABELLED WITH RADIOACTIVITY USED AS MEANS FOR TARGETING NEOPLASTIC CELLS

This application is a continuation-in-part of U.S. application Ser. No. 08/388,147 filed Feb. 13, 1995, now abandoned, which is a continuation of U.S. application Ser. No. 08/388,148, filed Feb. 13, 1995, now U.S. Pat. No. 5,578,583 which is a divisional of Ser. No. 08/042,105 filed Apr. 1, 1993 (now abandoned).

FIELD OF THE INVENTION

The present invention refers to a method for diagnosing neoplasms by injecting radioactive materials into the human body.

BACKGROUND OF THE INVENTION

LDL (low-density lipoprotein), a lipoprotein that exists in the plasma, is the main carrier of cholesterol in the human body. This lipoprotein consists of a quasispherical particle composed of a monolayer of phospholipids and cholesterol surrounding a nucleus of neutral lipids, chiefly composed of cholesterol esters and residual triglycerides. This LDL particle is usually found in the plasma associated with a protein molecule called apolipoprotein $B_{100}$ (apo B). This molecule is the ligand that will allow the LDL particle to be internalized by the LDL specific receptors located on the cell membrane. After binding to the LDL receptors, the LDL particle is internalized and degraded in lysosomes and its cholesterol is used in several cell processes, such as membrane synthesis. In other words, in order for the LDL particle to be recognized by its specific receptor, the particle must be associated with its linking element, the apo B. Thus, binding to the LDL receptor of the cell requires a stereochemical conformation of the apo B which is bound to the LDL particle. As such, a domain of the apo B molecule binds to the surface of the LDL particle, whereas another domain binds to the LDL specific receptor of the cell. This internalization by receptor-mediated endocytosis, conceivably requires the presence of the entire lipoprotein associated with the apo B molecule, thus not being triggered by the apo B alone.

It is known in the art that in rapidly proliferating malignant cells, the increased need of cholesterol for new membrane synthesis may result in an over expression of the LDL receptors, which allows a greater uptake of the LDL particles by those cells. This increase is expressed in several lineages of cancer diseases, such as acute myeloid leukemia, myeloproliferous diseases, glioma, endometrial carcinoma, carcinoma of the prostate, uterine carcinoma, cancer of the breast, cancer of the gall bladder, cancer of the renal cells and cancer of the lung. Depending on the lineage of the tumor, the number of LDL receptors can be 3 to 100 times increased, whereas normal cells, due to their low number of LDL receptors have nearly "closed gates" for internalization of the LDL particle.

Some kinds of microemulsions and their respective method for preparation have been previously described and are available in the literature (see Ginsburg et al., *Journal of Biological Chemistry*, 257:8216, 1982 and Reisinger and Atkinsons, *Journal of Lipid Research*, 31:849, 1990). In the last decade, several investigators suggested the possibility of using native LDL to shuttle antitumor drugs to cells, based on the increased expression of the LDL in certain types of cancer. Although this experiment proved successful, the difficulty in isolating the LDL from the plasma and handling the preparation thereof are serious drawbacks for its use in the treatment and diagnosis of cancer. Therefore, the use of native LDL for the above purposes remain confined to experimental trials. None of the prior art publications have suggested an artificially made protein-free microemulsion, capable of interacting with the LDL specific receptors and being applicable to a method for diagnosing cancer. Further, conventional methods for diagnosing or controlling the evolution of malignant tumors, such as tomography or conventional scintilography, are not capable of detecting the disease in its early stage or when the tumor is rather small in size.

SUMMARY OF THE INVENTION

It is an objective of this invention to provide a method for diagnosing neoplasms by means of injecting radioactively-labelled microemulsions into the blood circulation so as to localize neoplastic cells.

It is also an object of the present invention to provide a more accurate method for detecting the presence of tumoral processes in their early stage.

Another object of this invention is to provide a microemulsion that, when incorporated with greater amounts of radioactive materials, not only improves the quality of the images generated but also kills the neoplastic cells.

DETAILED DESCRIPTION OF THE INVENTION

By observing the receptor-mediated endocytosis mechanism of the cells, it has been discovered in accordance with this invention that an artificially prepared microemulsion, covered by a phospholipid monolayer resembling that of the native lipoprotein but without the protein molecule apo B, when injected into the plasma, mimics the metabolism of the native LDL and acquires, by collision with other native LDL particles (VLDL very low-density lipoprotein or HDL high-density lipoprotein), another protein (apo E), which may also be recognized and internalized by the LDL specific receptors. Differently from the apo B, apo E may exist in the plasma associated with the native VLDL/HDL or it may exist in its free form, whereas the apo B, an insoluble protein, is not prone to transferring from native LDL to the artificial microemulsion. Moreover, apo B does not exist in the plasma alone. Therefore, the artificially made microemulsion binds to the apo E molecule and is then recognized and internalized by the LDL receptors on the cells.

As these receptors are highly increased in neoplastic cells, these microemulsions, when labelled with radioactive materials and injected into the bloodstream, bind to the apo E molecule and are internalized in greater quantity by the neoplastic cells, reaching high concentrations in these cells, therefore allowing a more precise diagnosis of malignant tumors. This hypothesis has been confirmed in patients with acute myeloid leukemia (AML), a disease in which the LDL receptors are up to 100 times increased. The removal of the microemulsions, marked with a radioactive cholesterol ester from the plasma, was much faster than when the microemulsions were injected in normal individuals, compared to individuals with acute lymphocytic leukemia, a disease in which the expression of the LDL receptors is comparatively reduced. When the AML patients were treated, achieving the remission of the disease (a condition in which the cells with exceeding LDL receptors disappear), the removal of the microemulsions from the plasma normalized. This clearly shows that the microemulsions have the capacity of specific penetration into the neoplastic cells.

The method herein described can be more accurate than conventional methods for diagnosing or for follow-up of the evolution of the disease in view of the fact that cancer cells have high affinity for the microemulsion, due to the great number of LDL receptors which promote the microemulsion uptake by those cells. The microemulsion labelled with the radioactive materials can signal the presence of an early tumor when methods such as tomography or conventional scintilography are still not able to detect the presence of a tumoral process in its early stage.

This protein-free microemulsion consists of a substantially spherical particle surrounded by a monolayer of phospholipids and free cholesterol with a hydrophobic core basically constituted of cholesterol esters, or other neutral compounds. The microemulsion is then labelled with radioactivity using sodium dithionite as a reducing agent, shortly after it is prepared, in an aqueous medium, by exposing to ultrasound the lipids that form these microemulsions. The radioactively-labelled microemulsion complex is then purified by gel filtration or ultracentrifugation, and finally sterilized by filtration.

After the microemulsion is prepared and labelled, the microemulsion complex is injected intravenously into the patient under suspicion of bearing a malignant tumor within 30 minutes of the radiolabelling. Once in contact with the plasma, the microemulsion will gain apolipoprotein E from the blood circulation. Acquisition of apolipoprotein E will then enable the microemulsion particle to bind to the LDL specific receptors of the malignant cells, much more than in the normal cells. The radioactive label carried by the microemulsion is thus internalized into the cells. Images may be successfully registered by an external detecting means, such as gamma scintillation scanning for image acquisition, after 6 hours postinjection. Three different kinds of radioactive compounds may be incorporated into the microemulsions: $^{99m}Tc$, $^{123}I$, $^{131}I$. All three radioactive compounds are capable of improving the quality of the images generated. If the $^{131}I$ radioactive compound is incorporated into the radioactive material in greater amounts, when internalized into the neoplastic cells, it will be capable of killing these cells, thus also serving a therapeutic purpose.

Because the microemulsions mimic the metabolism of the LDL particles present in the blood circulation, in addition to being a toxic for the organism, they are capable of binding to the apo E molecule, thereby allowing the artificial particles labelled with radioactivity to be sequestrated into the cells by receptor-mediated endocytosis, regardless of the amount of radioactive materials incorporated into these microemulsions. Furthermore, incorporation of these compounds does not diminish the capacity of the microemulsions to incorporate apo E into the plasma and subsequently bind to the LDL receptors of the cells. In human subjects, no change has been observed in the kinetics of the radioactively labelled microemulsions. The concentration of apo E in the plasma is enough to bind many grams of the microemulsion and internalize the particles into the neoplastic cells.

To further illustrate the present invention, reference is made to the following example. It should be understood that the invention is not limited to the specific examples or details described therein.

Example

In some gamma camera images acquired 6 hours postinjection, the biodistribution of radioactively-labelled microemulsions in one ALL (acute lymphocytic leukemia) patient and one AML (acute myeloid leukemia) nontreated patient was observed. In the ALL patient, the liver was the predominant uptake site. The microemulsion uptake by the liver was markedly lower in the AML patient, compared with the ALL patient. On the other hand, the radioisotope activity was pronouncedly higher in the AML patient over the areas corresponding to the pelvic bones, femur, and skull, the sites presumably containing bone marrow invaded by the malignant cells.

The microemulsion removal from the plasma of the ALL patient equaled that of normolipidemic healthy subjects, as observed in 19 healthy volunteers. Moreover, the radioactive images acquired in the ALL patient resembled those obtained from two healthy subjects. Again, the microemulsion behaved like LDL, since the images obtained from the ALL patient and the two controls were similar to those obtained with radioactivity, the liver being the main uptake organ. In the AML patient the lower hepatic uptake of the radioactively-labelled microemulsion associated with enhanced uptake over the bone marrow areas was expected.

Therefore, the clearcut results obtained by the method proposed herein fully confirm that the microemulsion can be a preparation perfectly suitable for targeting the neoplastic cells. It is easy to prepare from materials produced by the chemical industry; radioactive materials can be easily incorporated into these microemulsions by cosonication with the lipid mixtures or incubation with the formed emulsion. When stored at 4° C., the microemulsion can be preserved for a longer period.

The microemulsion described hereinabove was prepared in accordance with the method proposed by Ginsburg et al., *Journal of Biological Chemistry*, 257:8216–8227 (1982) and modified by the inventor. Egg phosphatidylcholine, triolein, cholesteryl oleate and radioactive lipids were purchased. Lipids were >98% pure as determined by thin layer chromatography. The microemulsion was prepared from lipid mixtures composed of 40 mg of phosphatidylcholine, 20 mg of cholesteryl oleate, 1 mg of triolein, and 0.5 mg of unesterified cholesterol. All the materials and instruments used in the preparation of the emulsion were put into an oven at 180° C. for 4 hours and subsequently autoclaved. Lipids were dissolved in a solution consisting of chloroform:methanol (2:1) and subsequently dispensed into vials. The mixtures were dried under a nitrogen stream followed by overnight vacuum desiccation at 4° C. to remove residual solvents. The dried lipids were resuspended in 10 ml of a mixture containing 0.1M KCl and 0.01M Tris-HCl, and having a pH of 8.0. The suspension was sonicated using a Branson model 450 cell disrupter, with a 125-W output in the "continuous" operating mode, for 180 minutes under $N_2$ atmosphere. The temperature was kept above 52° C., the melting point of cholesterol oleate, as monitored by a thermocouple inserted in the vials during this procedure. The emulsified lipid suspension was then transferred to clean tubes for ultracentrifugation at 195,000×g for 30 minutes in a TH 641 rotor of an ultracentrifuge at 4° C. The top 10% of the solution, containing particles that float at background density of approximately 1.006 g/ml, was removed by aspiration with a needle. The remaining solution was adjusted to a background density of 1.22 g/ml by adding solid KBr. A second ultracentrifugation step was then performed at 195,000×g for 120 minutes at 4° C. The top 20–30% of the sample was collected by aspiration, after attaining room temperature and dialyzed overnight in Tris-HCl buffer to remove KBr contained in the solution. This emulsion fraction was sterilized by passing it through a 0.2 μm filter and analyzed for lipid composition by standard laboratory methods. The microemulsion prepared as described had approximately 64% phospholipids, 33% cholesterol ester, 1% unesterified cholesterol, and 2% triacylglycerols. The microemulsion was used in experiments within one week after it was prepared.

The microemulsion was labelled with $^{99m}$Tc for imaging of its biodistribution, using sodium dithionite as a reducing agent. The $^{99m}$Tc-emulsion complex was purified by gel filtration and sterilized by passing it through a 0.2 μm filer. The $^{99m}$Tc-emulsion (370 MBq) was injected intravenously into subjects within 30 minutes of radiolabelling. As tested by thin-layer chromatography, 90% of the radiation was found at the microemulsion phospholipids. The planar images were obtained in anterior and posterior views 6 h postinjection of 370 MBq $^{99m}$Tc-emulsion. Digitized images of a view gamma camera (Siemens-Basicam, Des Plaines, Ill.) equipped with a general-purpose parallel-hole collimator were stored in 128×128 matrices in a dedicated computer system and analyzed later.

What is claimed is:

1. A method for diagnosing neoplasms, wherein cells from said neoplasms have an increased number of LDL receptors, comprising:
   a. injecting intravenously into the plasma of a person a protein-free microemulsion, composed of particles having a hydrophobic core surrounded by a monolayer of phospholipids having free cholesterol on the surface of said phospholipids, said particles labelled with a detectable amount of radioactive material bound to said phospholipids and the hydrophobic core;
   b. binding the surface of said particles to apolipoprotein E circulating in the plasma;
   c. binding said apolipoprotein E bound to said particles to the LDL specific receptor on said neoplastic cells; and,
   d. detecting said particles bound to said apolipoprotein E and LDL receptor, allowing said radioactive material to be registered by a detecting means external to the person.

2. The method of claim 1, wherein said neoplasms to be diagnosed are myeloproliferative diseases, glioma, endometrial carcinoma, prostate carcinoma, uterine carcinoma, breast cancer, gall bladder cancer, lung cancer and renal cell carcinoma.

3. The method of claim 2, wherein said myeloproliferative disease to be diagnosed is myeloid leukemia.

4. The method of claim 1, wherein said radioactive material is selected from the group consisting of $^{99m}$Tc, $^{123}$I, $^{131}$I.

5. The method of claim 1, wherein said hydrophobic core of said particles consists essentially of either cholesterol esters, triglycerides, or mixtures thereof.

6. The method of claim 1, wherein the detectable amount of said radioactive material incorporated into said microemulsion is increased to an amount sufficient to kill said neoplastic cells.

* * * * *

UNITED STATES PATENT AND TRADEMARK OFFICE
CERTIFICATE OF CORRECTION

PATENT NO. : 5,874,059
DATED : February 23, 1999
INVENTOR(S) : Raul Cavalcante MARANHAO It is certified that error appears in the above-identified patent and that said Letters Patent is hereby corrected as shown below:

On the title page of the patent, Section [73], as follows:

Delete "Fundacao E. J. Zerbini" and insert therefor -- Fundação E. J. Zerbini --

Signed and Sealed this

Second Day of May, 2000

Q. TODD DICKINSON

*Attest:*

*Attesting Officer*     *Director of Patents and Trademarks*